US00PP11667P

United States Patent [19]

Klemm

[11] Patent Number: Plant 11,667

[45] Date of Patent: Dec. 5, 2000

[54] GERANIUM PLANT NAMED 'KLEMET'

[75] Inventor: Siegfried Klemm, Stuttgart, Germany

[73] Assignee: Klemm & Sohn, Stuttgart, Germany

[21] Appl. No.: 09/250,021

[22] Filed: Feb. 12, 1999

[51] Int. Cl.[7] ..... A01H 5/00

[52] U.S. Cl. ..... Plt./332

[58] Field of Search ..... Plt./332

*Primary Examiner*—Howard J. Locker
*Assistant Examiner*—Wendy A Baker
*Attorney, Agent, or Firm*—C. A. Whealy

[57] ABSTRACT

A new and distinct cultivar of Ivy Geranium plant named 'Klemet', characterized by its numerous semi-double dark red-colored flowers; trailing, compact and bushy plant habit; vigorous and freely branching growth habit; and medium green leaves.

1 Drawing Sheet

BACKGROUND OF THE INVENTION

The present invention relates to a new and distinct cultivar of Ivy Geranium plant, botanically known as *Pelargonium peltatum* and hereinafter referred to by the cultivar name Klemet.

The new Ivy Geranium is a product of a planned breeding program conducted by the Inventor in Stuttgart, Germany. The objective of the breeding program was to develop new cultivars with good cutting production, red flower color, strong plant growth, and medium growth habit.

The new Ivy Geranium originated from a cross made by the Inventor of an unidentified proprietary *Pelargonium peltatum* selection as the male, or pollen parent, with the *Pelargonium peltatum* cultivar Gaugin, not patented, as the female, or seed parent. The cultivar Klemet was discovered and selected by the Inventor as a flowering plant within the progeny of the stated cross in a controlled environment in Stuttgart, Germany in 1994.

Asexual reproduction of the new cultivar by terminal cuttings taken at Stuttgart, Germany, has shown that the unique features of this new Ivy Geranium are stable and reproduced true to type in successive generations of asexual reproduction.

SUMMARY OF THE INVENTION

The following traits have been repeatedly observed and are determined to be the unique characteristics of 'Klemet'. These characteristics in combination distinguish 'Klemet' as a new and distinct cultivar:

1. Numerous semi-double dark red-colored flowers.
2. Trailing, compact and bushy plant habit.
3. Vigorous and freely branching growth habit.
4. Medium green leaves.

Compared to plants of the parent Ivy Geraniums, plants of the new Ivy Geranium produce more cuttings per plant and have a darker red flower color.

The new Ivy Geranium can also be compared to the commercial cultivar Klefeli, disclosed in U.S. Plant Pat. No. 8,885. However in side-by-side comparisons conducted in Stuttgart, Germany, plants of the new Ivy Geranium are more compact and have a brighter flower color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical plant of 'Klemet'. Flower and foliage colors in the photograph may appear different from the actual colors due to light reflectance.

DETAILED BOTANICAL DESCRIPTION

The cultivar Klemet has not been observed under all possible environmental conditions. The phenotype may vary somewhat with variations in environment such as temperature and light intensity, without, however, any variance in genotype. The following observations, measurements and comparisons describe plants grown in Stuttgart, Germany, under commercial greenhouse conditions.

In the following description, color references are made to The Royal Horticultural Society Colour Chart except where general terms of ordinary dictionary significance are used.

Botanical classification: *Pelargonium peltatum* cultivar Klemet.

Parentage:

- *Male parent.*—Unidentified proprietary *Pelargonium peltatum* selection.
- *Female parent.*—*Pelargonium peltatum* cultivar Gaugin, not patented.

Propagation:

- *Type cutting.*—Terminal cuttings.
- *Time to develop roots.*—About 18 to 20 days.
- *Rooting habit.*—Fibrous and freely branching.

Plant description:

- *General appearance.*—Trailing, compact and bushy plant habit; vigorous; freely flowering.
- *Crop time.*—About 95 to 100 days are required to produce a finished flowering plant from a rooted cutting.
- *Growth and branching habit.*—Moderate growth rate; vigorous; freely branching with about four stalks with about two to three stems. Removal of terminal apices (pinching) will enhance branching.
- *Plant height to top of umbels.*—About 20 to 25 cm.
- *Stem length.*—About 13 to 18 cm.
- *Internode length.*—About 3 to 4 cm.
- *Foliage description.*—Leaves simple, medium sized, generally symmetrical, abundant, opposite, leathery. Shape: Peltate with weakly crenated margin. Color: Fully expanded foliage, upper surface: 137B. Fully expanded foliage, lower surface: 137C. Petiole length: About 3 to 6 cm.

Flower description:

- *Flower type and habit.*—Dark red-colored flowers. Very freely and continuously flowering. Flowers arranged in umbels arising from apical leaf axils. Umbels elliptic in shape. Umbels displayed above or beyond the foliage. Flowers semi-double. Umbels persistent.

*Flowering season.*—Year-round under greenhouse conditions. In the garden, flowering is continuous from spring through summer.

*Quantity of inflorescences.*—Typically about 2 to 3 umbels per lateral stem with about 180 to 200 umbels per plant forming during the flowering season.

*Lasting quality.*—Flowers last about 10 to 14 days on the plant and about 4 to 5 days as cut flowers.

*Fragrance.*—None.

*Umbels.*—Diameter: About 10 cm. Height: About 8 to 9 cm.

*Flowers.*—Quantity per inflorescence: About 10 to 15. Diameter: About 6 to 6.5 cm. Shape: Rounded, mostly flat.

*Flower buds.*—Length: About 1.5 to 2 cm. Diameter: About 1.2 to 1.5 cm. Shape: Ovoid, pointed.

*Petals/petaloids.*—Quantity: About 8 to 10 petals and about 3 to 8 petaloids. Arrangement: Imbricate. Shape: Rounded apex and entire margin. Texture: Smooth. Color: Outer petals, fully opened, upper surface: 45A. Outer petals, fully opened, lower surface: 46B to 46C. Inner petals and petaloids, fully opened, upper surface: 45A. Inner petals and petaloids, fully opened, lower surface: 45C.

*Sepals.*—Quantity: About five. Shape: Elongated, pointed. Angle: Upright. Color: Outer surface: 137C. Inside surface: 137D.

*Pedicel.*—Length: About 1.8 to 2.5 cm. Strength: Moderate. Angle: Mostly upright. Color: Greenish brown.

*Reproductive organs.*—Androecium: Stamens: Typically four or five. Anther size: About 2 mm. Anther color: Dark red-orange. Filament length: About 7 to 8 mm. Filament color: Light purple. Pollen color: Orange. Gynoecium: Pistils: Typically one with four or five branches. Style length: About 4 to 6 mm. Style color: Green. Stigma color: Purple.

*Seed.*—Length: about 3 to 4.5 mm. Color: Brown.

Disease resistance: Under commercial conditions, resistance to Botrytis has been observed.

Weather tolerance: Flowers of plants of the new Ivy Geranium have been observed to be tolerant to wet and hot conditions.

It is claimed:

1. A new and distinct cultivar of Ivy Geranium plant named 'Klemet', as illustrated and described.

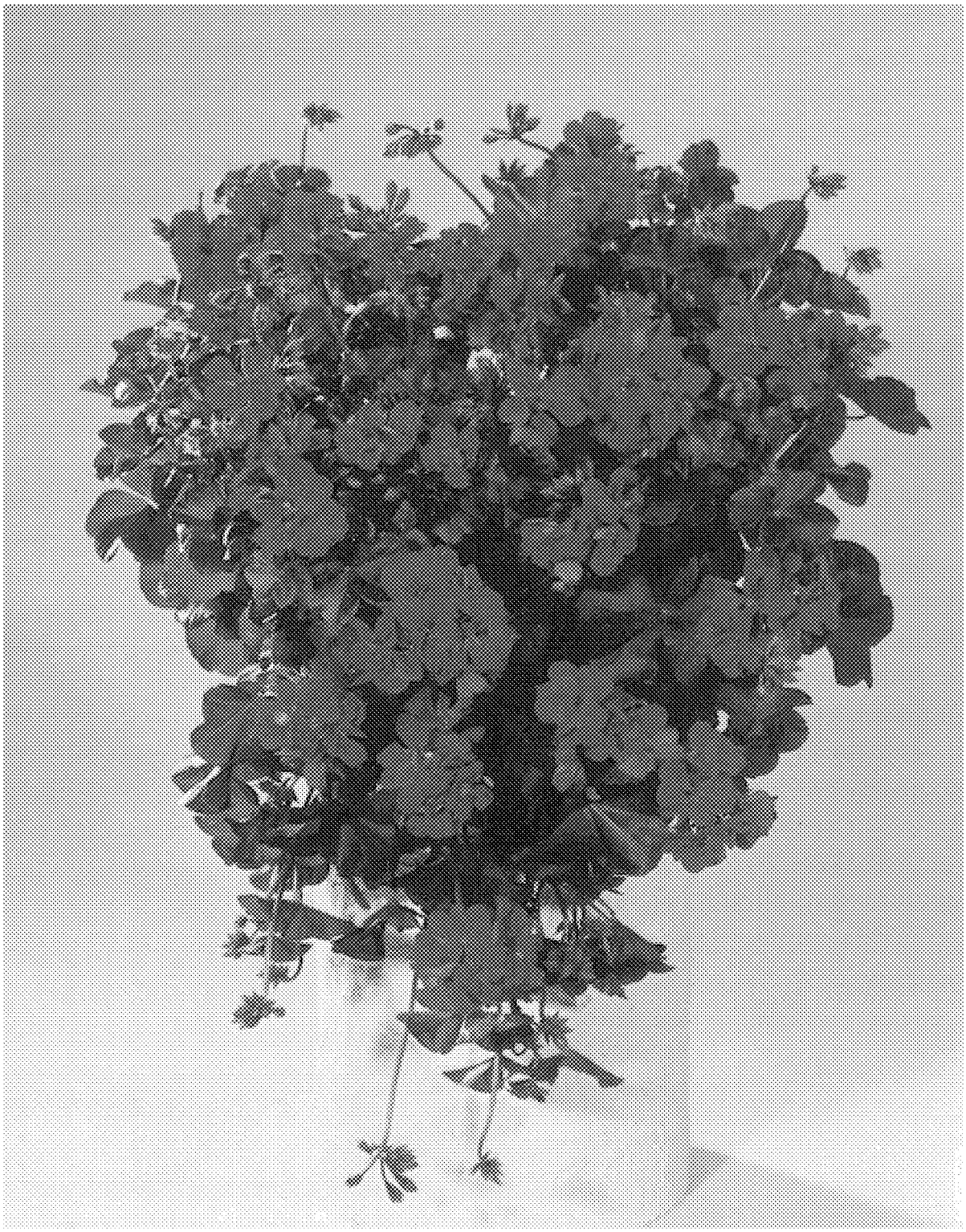

* * * * *